United States Patent [19]

Seido et al.

[11] Patent Number: 5,081,310

[45] Date of Patent: Jan. 14, 1992

[54] PROCESS FOR PREPARING OPTICALLY ACTIVE KETONES

[75] Inventors: Nobuo Seido; Hidenori Kumobayashi, both of Kanagawa, Japan

[73] Assignee: Takasago International Corporation, Tokyo, Japan

[21] Appl. No.: 553,285

[22] Filed: Jul. 17, 1990

[30] Foreign Application Priority Data

Jul. 17, 1989 [JP] Japan .................... 1-182442

[51] Int. Cl.$^5$ .............................. C07C 45/62
[52] U.S. Cl. .................................... 568/350
[58] Field of Search .............. 568/350; 550/18, 21

[56] References Cited

U.S. PATENT DOCUMENTS

| | | | |
|---|---|---|---|
| 3,930,952 | 1/1976 | Greenspan et al. | 568/350 |
| 4,041,083 | 8/1977 | Gradeff et al. | 568/350 |
| 4,147,727 | 4/1979 | Sprecker et al. | 568/330 |
| 4,260,830 | 4/1981 | Wilson et al. | 568/350 |
| 4,691,037 | 9/1987 | Yashikawa et al. | 556/21 |
| 4,766,227 | 8/1988 | Sayo et al. | 556/21 |
| 4,916,252 | 8/1988 | Sayo, et al. | 568/350 |
| 4,933,482 | 6/1988 | Sayo et al. | 568/350 |

FOREIGN PATENT DOCUMENTS

| | | | |
|---|---|---|---|
| 174057 | 12/1986 | European Pat. Off. | 568/350 |
| 61-30545 | 2/1986 | Japan | 568/350 |

OTHER PUBLICATIONS

Ikariya et al., J. Chem. Soc., Chem. Comm., pp. 922–924 (1985).

*Primary Examiner*—James H. Reamer
*Attorney, Agent, or Firm*—Sughrue, Mion, Zinn Macpeak & Seas

[57] ABSTRACT

A process for preparing an optically active ketone represented by formula (I):

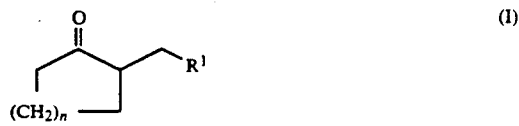

wherein $R^1$ represents a hydrogen atom or an alkyl group having from 1 to 5 carbon atoms; and n represents 1 or 2, which comprises asymmetrically hydrogenating an α, β-unsaturated ketone represented by formula (II):

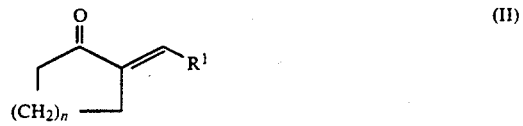

wherein $R^1$ and n are as defined above, in the presence of a ruthenium-optically active phosphine complex as a catalyst. An optically active ketone having a high optical purity can be prepared.

6 Claims, No Drawings

PROCESS FOR PREPARING OPTICALLY ACTIVE KETONES

FIELD OF THE INVENTION

This invention relates to a process for preparing an optically active ketone useful as an intermediate for synthesizing prostaglandins, xanthine derivatives, etc.

BACKGROUND OF THE INVENTION

Known processes for asymmetrically synthesizing optically active ketones include (1) a process comprising asymmetric hydrogenation in the presence of a specific catalyst and (2) a process utilizing a hydrogenation reaction by the action of an enzyme.

In particular, known processes for preparing optically active ketones having a cyclopentanone or cyclohexanone skeleton include a process in which an $\alpha,\beta$-unsaturated ketone is asymmetrically hydrogenated by using, for example, a chiral ruthenium hydride complex containing trans-1,2-bis(diphenylphosphinomethyl)cyclobutane (hereinafter abbreviated as TBPC) (e.g., HRuCl(TBPC)$_2$, H$_2$Ru(TBPC)$_2$). For example, where an $\alpha,\beta$-unsaturated ketone as a substrate has a double bond subject to reduction in its ring (endo-form), isophorone (i.e., 3,5,5-trimethyl-2-cyclohexen-1-one), 3-methyl-2-cyclohexen-1-one, 2-methyl-2-cyclohexen-1-one, or 3-methyl-2-cyclopenten-1-one gives an optically active ketone having an optical purity of 62% ee, 22% ee, 26% ee, or 4.5% ee, respectively. Where a substrate has a double bond subject to reduction outside the ring thereof (exo-form), $\alpha$-methylenetetralone (i.e., 3,4-dihydro-2-methylene-1-naphthalenone) gives an optically active ketone having an optical purity of 23% ee. Reference can be made to V. Massonneau, et al., *Tetrahedron Letters*, Vol. 27, (45), pp. 5497–5498 (1986).

An example of the process of using an enzyme is described in A. Kergomard, et al., *J. Org. Chem.*, Vol. 47, pp. 792–798 (1982), in which 2-methyl-2-cyclohexen-1-one is reduced with Beauveria sulfurescens to obtain an optically active ketone having an R-configuration at the 2-position in a percent yield of 30%.

In the field of synthesis of pharmaceuticals, a process for synthesizing 11-deoxyprostaglandin E comprising asymmetrically reducing prostaglandin A as a typical $\alpha,\beta$-unsaturated cyclopentenone by using a microorganism is reported in U.S. Pat. No. 3,930,952.

Further, it has been proposed to biologically reduce oxoisophorone to obtain (4R,6R)-4-hydroxy-2,2,6-trimethyl-cyclohexanone which is an intermediate for synthesizing astaxanthin which is a kind of carotenoid, xanthine, or loliolide as described in R. Zell, et al., *Helv. Chim. Acta*, Vol. 59, p. 1832 (1976).

However, the conventional processes comprising asymmetric hydrogenation using a metal complex, e.g., HRuCl(TBPC)$_2$, as a catalyst find difficulty in obtaining an optically active ketone having a satisfactorily high optical purity.

In the case of the processes using an enzyme, on the other hand, the steric configuration of a product obtained is limited in many cases. In addition, these processes involve complicated procedures for separating the product from microbial cells.

It has been therefore demanded to develop a process for effectively obtaining an optically active ketone with a high optical purity.

SUMMARY OF THE INVENTION

In the light of the above-described situation, the present inventors have conducted extensive investigations. As a result, it has now been found that an optically active ketone having a high optical purity can be prepared with good efficiency by asymmetrically hydrogenating an $\alpha,\beta$-unsaturated ketone represented by formula (II) shown below in the presence of a specific ruthenium-optically active phosphine complex as a catalyst. The present invention has been completed based on this finding.

The present invention provides a process for preparing an optically active ketone represented by formula (I):

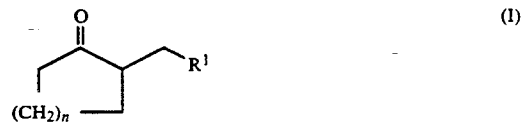

wherein R$^1$ represents a hydrogen atom or an alkyl group having from 1 to 5 carbon atoms; and n represents 1 or 2, which comprises asymmetrically hdyrogenating an $\alpha,\beta$-unsaturated ketone represented by formula (II):

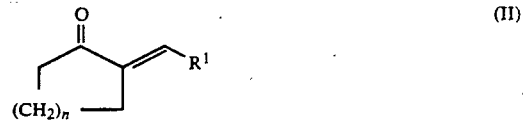

wherein R$^1$ and n are as defined above, in the absence of a ruthenium-optically active phosphine complex as a catalyst.

DETAILED DESCRIPTION OF THE INVENTION

The $\alpha,\beta$-unsaturated ketone of formula (II) which can be used as a substrate in the process of this invention includes 2-methylenecyclopentanone, 2-ethylidenecyclopentanone, 2-propylidenecyclopentanone, 2-pentylidenecyclopentanone, 2-(2-methyl)propylidenecyclopentanone, 2-(3-methyl)butylidenepentanone, 2-methylenecyclohexanone, 2-butylidenecyclohexanone, 2-pentylidenecyclohexanone, 2-hexylidenecyclohexanone, 2-(2-methyl)propylidenecyclohexanone, and 2-(4-methyl)pentylidenecyclohexanone. These compounds can be synthesized, for example, by condensing a 5- or 6-membered ketone with an aldehyde according to the process disclosed, e.g., in U.S. Pat. No. 4,260,830.

The ruthenium-optically active phosphine complex which can be used as a catalyst in the present invention includes those represented by formulae (III) and (V) shown below.

In formula (III), R$^2$-BINAP represents a tertiary phosphine represented by formula (IV):

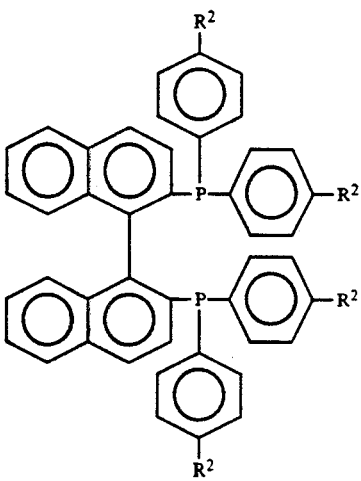

wherein $R^2$ represents a hydrogen atom, a methyl group, or a t-butyl group; and Et represents an ethyl group.

$$[RuX(Q)(R^2\text{-BINAP})]Y \quad (V)$$

In formula (V), $R^2$-BINAP is as defined above; X represents a chlorine atom, a bromine atom, or an iodine atom; Q represents a substituted or unsubstituted benzene ring; and Y represents a chlorine atom, a bromine atom, an iodine atom, $ClO_4$, $BF_4$, or $PF_6$.

The ruthenium-optically active phosphine complex represented by formula (III) can be obtained, for example, by the processes disclosed in T. Ikariya, et al., *J. Chem. Soc., Chem. Commun.*, pp. 922-924 (1985) and JP-A-61-63690 (the term "JP-A" as used herein means an "unexamined published Japanese patent application"). In more detail, ruthenium chloride and cycloocta-1,5-diene (hereinafter abbreviated as COD) are reacted in an ethanol solution to form $[RuCl_2(COD)]_m$, which is then heated in a solvent, e.g., toluene or ethanol, in the presence of triethylamine to obtain the complex of formula (III).

Specific examples of the ruthenium-optically active phosphine complex of formula (III) are shown below.

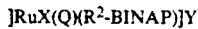

(wherein BINAP represents 2,2'-bis(diphenyl-phosphino)-1,1'-binaphthyl)

(wherein Tol-BINAP represents 2,2'-bis(di-p-tolylphosphino)-1,1'-binaphthyl)

(wherein t-Bu-BINAP represents 2,2'-bis(di-p-t-butylphenylphosphino)-1,1'-binaphthyl)

The ruthenium-optically active phosphine complex represented by formula (V) can be obtained, for example, by the process described in *Dai 35-kai Yuki Kinzoku Toronkai Yoshishu*, pp. 37-39 (1988). That is, the compound of formula (V) wherein X and Y both represent a chlorine atom, a bromine atom, or an iodine atom can be prepared as follows taking the compound wherein X and Y both represent a chlorine atom, i.e., [RuCl(Q)(BINAP)]Cl, as an instance. $[RuCl_2(Q)]_2$, which is prepared by a known process, e.g., the process described in G. Wikhaus, *J. Org. Chem.*, Vol. 7, p. 487 (1976) or R. A. Zelonka, *Can. J. Chem.*, Vol. 50, p. 3643 (1972), is reacted with BINAP in a solvent, e.g., methanol. The compound of formula (V) wherein X is a chlorine atom, a bromine atom, or an iodine atom (a chlorine atom is taken as an example), and Y is $ClO_4$, $PF_6$, or $BF_4$, can be obtained, for example, by dissolving [RuCl(Q)(BINAP)]Cl in a solvent, e.g., methanol, and adding a salt represented by MY (wherein M represents Na, K, Li, Mg, or Ag; and Y is as defined above) to the solution to conduct a reaction.

Specific examples of the ruthenium-optically active phosphine complex of formula (V) are shown below.

[RuCl(benzene)(BINAP)]Cl
[RuCl(benzene)(Tol-BINAP)]Cl
[RuCl(p-cymene)(BINAP)]Cl
[RuCl(methyl benzoate)(BINAP)]Cl
[RuBr(benzene)(BINAP)]Br
[RuI(benzene)(Tol-BINAP)]I
[RuI(p-cymene)(BINAP)]I
[RuCl(p-cymene)(BINAP)]ClO_4
[RuCl(benzene)(BINAP)]BF_4
[RuI(p-cymene)(BINAP)]PF_6

The phosphine derivative in each of the above-enumerated ruthenium-optically active phosphine complexes is either one of enantiomers thereof, though not shown.

In carrying out the present invention, a rutheniumoptically active phosphine complex is put in an autoclave whose atmosphere has previously been displaced with nitrogen, and an $\alpha\beta$-unsaturated ketone is added thereto in an amount of from 10 to 5,000 molar times, preferably from 20 to 500 molar times, the complex. At least one solvent selected from an alcohol, e.g., methanol, ethanol, and isopropanol, and a halogenated compound, e.g., methylene chloride, 1,2-dichloroethane, and trichloroethylene, is further added thereto to form a uniform solution. The reaction system is subjected to hydrogenation at a hydrogen pressure of from 10 to 150 kg/cm², preferably from 30 to 100 kg/cm², and at a temperature of from 10° to 100° C., preferably from 40° to 60° C., for a period of from 10 to 150 hours, preferably from 20 to 120 hours. After the reaction, the solvent is removed by distillation, and the residue is then subjected to distillation or silica gel column chromatography to isolate the desired optically active ketone.

In the present invention, an optically active ketone having a desired absolute configuration can be obtained by accordingly selecting the absolute configuration (i.e., (+)-form or (−)-form) of a ruthenium-optically active phosphine complex to be used.

The present invention is now illustrated in greater detail by way of the following Examples, but it should be understood that the present invention is not construed as being limited thereto In Examples, the structure of reaction products was decided by ¹H-NMR analysis using Model JNM-GX 400 (400 MHz) manufactured by JEOL Ltd.; and the optical purity of compounds was determined by high-performance liquid chromatography (HPLC) according to the following conditions.

Chromatograph: L-6000, manufactured by Hitachi, Ltd.
Column: CHIRAL CEL OJ (4.6 mm (d)×250 mm (h)), manufactured by Daicel Chemical Industries, Ltd.

Developing Solvent: Isopropanol:hexane=3:7 (by volume); flow rate: 1 ml/min
UV Detector: L-4000 (UV wavelength: 210 nm), manufactured by Hitachi, Ltd.

EXAMPLE 1

Synthesis of (+)-2-Pentylcyclopentanone

In a 100 ml-volume three-way-cocked eggplant type flask whose atmosphere had been displaced with nitrogen was charged 270 mg (0.16 mmole) of $Ru_2Cl_4((+)\text{-}BINAP)_2(NEt_3)$, and 5 g (32 mmole) of 2-pentylidenecyclopentanone and 50 ml of methylene chloride were added thereto to form a solution. The solution was put in a 100 ml autoclave having been displaced with nitrogen and stirred at 50° C. under a hydrogen pressure of 60 kg/cm² for 20 hours to conduct a hydrogenation reaction. The solvent was removed from the reaction mixture by distillation, and the residue was purified by silica gel column chromatography using a mixed solvent of diethyl ether and hexane (1:4 by volume) as an eluent to obtain 5 g (percent yield: 100%) of 2-pentylcyclopentanone as a clear yellow liquid.

$^1$H-NMR (CDCl$_3$)δ(ppm): 0.95 (t, 3H, J=5 Hz), 1.3 (m, 8H), 1.45–2.32 (m, 7H)

As a result of HPLC, the resulting product was found to be a mixture consisting of 98% of (+)-2-pentylcyclopentanone and 2% of (−)-2-pentylcyclopentanone, and the optical purity of the desired product, (+)-2-pentylcyclopentanone, was found to be 96% ee.

EXAMPLE 2

Synthesis of (+)-2-Pentylcyclopentanone

In a 100 ml-volume three-way-cocked eggplant type flask whose atmosphere had been displaced with nitrogen was charged 230 mg (0.14 mmole) of $Ru_2Cl_4((+)\text{-}BINAP)_2(NEt_3)$, and 5 g (32 mmole) of 2-pentylidenecyclopentanone and 50 ml of methanol were added thereto to form a solution. The solution was put in a 100 ml autoclave having been displaced with nitrogen and stirred at 50° C. under a hydrogen pressure of 90 kg/cm² for 110 hours to conduct a hydrogenation reaction. The solvent was removed from the reaction mixture by distillation, and the residue was purified by silica gel column chromatography using a mixed solvent of diethyl ether and hexane (1:4 by volume) as an eluent to obtain 4.6 g (percent yield: 92%) of 2-pentylcyclopentanone.

As a result of HPLC, the optical purity of the desired product, (+)-2-pentylcyclopentanone, was found to be 62% ee.

EXAMPLE 3

Synthesis of (+)-2-Pentylcyclopentanone

In a 100 ml-volume three-way-cocked eggplant type flask whose atmosphere had been displaced with nitrogen was charged 735 mg (0.66 mmole) of [RuI(p-cymene)((+]-BINAP)]I, and 2.5 g (16 mmole) of 2-pentylidenecyclopentanone and 50 ml of methylene chloride were added thereto to form a solution. The solution was put in a 100 ml autoclave having been displaced with nitrogen and stirred at 50° C. under a hydrogen pressure of 60 kg/cm² for 113 hours to conduct a hydrogenation reaction. The solvent was removed from the reaction mixture by distillation, and the residue was purified by silica gel column chromatography using a mixed solvent of diethyl ether and hexane (1:4 by volume) as an eluent to obtain 1.7 g (percent yield 67%) of 2-pentylcyclopentanone.

As a result of HPLC, the optical purity of the desired product, (+)-2-pentylcyclopentanone, was found to be 85% ee.

EXAMPLE 4

Synthesis of (+)-2-Propylcyclopentanone

In a 100 ml-volume three-way-cocked eggplant type flask whose atmosphere had been displaced with nitrogen was charged 845 mg (0.5 mmole) of $Ru_2Cl_4((+)\text{-}BINAP)_2(NEt_3)$, and 12.4 g (100 mmole) of 2-propylidenecyclopentanone and 50 ml of methylene chloride were added thereto to form a solution. The solution was put in a 100 ml autoclave having been displaced with nitrogen and stirred at 50° C. under a hydrogen pressure of 90 kg/cm² for 28 hours to conduct a hydrogenation reaction. The solvent was removed from the reaction mixture by distillation, and the residue was purified by silica gel column chromatography using a mixed solvent of diethyl ether and hexane (1:4 by volume) as an eluent to obtain 12 g (percent yield: 97%) of 2-propylcyclopentanone as a clear yellow liquid.

$^1$H-NMR (CDCl$_3$)δ(ppm): 1.50 (t, 3H, J=7 Hz), 1.42 (m, 4H), 1.50–2.80 (m, 7H)

As a result of HPLC, the optical purity of the desired product, (+)-2-propylcyclopentanone, was found to be 84% ee.

EXAMPLE 5

Synthesis of (+)-2-Ethylcyclopentanone

In a 100 ml-volume three-way-cocked eggplant type flask whose atmosphere had been displaced with nitrogen was charged 845 mg (0.5 mmole) of $Ru_2Cl_4((+)\text{-}BINAP)_2(NEt_3)$, and 11 g (100 mmole) of 2-ethylidenecyclopentanone and 50 ml of methylene chloride were added thereto to form a solution. The solution was put in a 100 ml autoclave having been displaced with nitrogen and stirred at 50° C. under a hydrogen pressure of 90 kg/cm² for 25 hours to conduct a hydrogenation reaction. The solvent was removed from the reaction mixture by distillation, and the residue was purified by silica gel column chromatography using a mixed solvent of diethyl ether and hexane (1:4 by volume) as an eluent to obtain 10.5 g (percent yield: 95%) of 2-ethylcyclopentanone as a clear yellow liquid. $^1$H-NMR (CDCl$_3$)δ(ppm): 1.20 (t, 3H, J=7 Hz), 1.40–2.80 (m, 9H)

As a result of HPLC, the optical purity of the desired product, (+)-2-ethylcyclopentanone, was found to be 75% ee.

EXAMPLE 6

Synthesis of (+)-2-Pentylcyclohexanone

In a 100 ml-volume three-way-cocked eggplant type flask whose atmosphere had been displaced with nitrogen was charged 845 mg (0.5 mmole) of $Ru_2Cl_4((+)\text{-}BINAP)_2(NEt_3)$, and 17.8 g (100 mmole) of 2-pentylidenecyclohexanone and 50 ml of methylene chloride were added thereto to form a solution. The solution was put in a 100 ml autoclave having been displaced with nitrogen and stirred at 50° C. under a hydrogen pressure of 90 kg/cm² for 23 hours to conduct a hydrogenation reaction. The solvent was removed from the reaction mixture by distillation, and the residue was purified by silica gel column chromatography- using a mixed solvent of diethyl ether and hexane (1:4 by volume) as an eluent to obtain 16 g (percent yield: 90%) of 2-pentylcyclohexanone as a clear yellow liquid. $^1$H-NMR (CDCl$_3$)δ(ppm): 1.20 (t, 3H, J=7 Hz), 1.40 (m, 8H), 1.50–2.50 (m, 9H)

As a result of HPLC, the optical purity of the desired product, (+)-2-pentylcyclohexanone, was found to be 90% ee.

EXAMPLE 7

Synthesis of (+)-2-Methylcyclohexanone

In a 100 ml-volume three-way-cocked eggplant type flask whose atmosphere had been displaced with nitrogen was charged 77 mg (0.046 mmole) of Ru$_2$Cl$_4$((+)-BINAP)$_2$(NEt$_3$), and 1 g (9.1 mmole) of 2-methylenecyclohexanone and 30 ml of methanol were added thereto to form a solution. The solution was put in a 100 ml autoclave having been displaced with nitrogen and stirred at 50° C. under a hydrogen pressure of 80 kg/cm$^2$ for 65 hours to conduct a hydrogenation reaction. The solvent was removed from the reaction mixture by distillation, and the residue was purified by silica gel column chromatography using a mixed solvent of diethyl ether and hexane (1:3 by volume) as an eluent to obtain 500 mg (percent yield: 50%) of 2-methylcyclohexanone as a clear yellow liquid. $^1$H-NMR (CDCl$_3$)δ(ppm): 1.0 (d, 3H, J=7 Hz), 1.2–2.5 (m, 9H)

Optical rotation of the resulting 2-methylcyclohexanone was found to be $[\alpha]_D^{25} = +11.7°$ (c=1.20, methanol) as measured by means of a polarimeter DIP-360 (manufactured by Nippon Bunko Kogyo K.K.). On comparing this result with the value of a reference, G. Simonneaux, *Tetrahedron Letters*, Vol. 27, (45), pp. 5497–5498 (1986), the optical purity of the above-prepared compound was found to be 78% ee.

As described above, the present invention provides a process for advantageously preparing an optically active ketone which is useful as an intermediate for synthesizing pharmaceuticals, such as prostaglandins having a variety of physiological properties including vasodilatory activity, and xanthine derivatives having cardiotonic diuretic activity and central nervous system exciting activity. That is, the process of the present invention provides an optically active ketone having a higher optical purity than that attained in the conventional techniques, by the use of a specific rutheniumoptically active phosphine complex as a catalyst in asymmetric hydrogenation and is, therefore, industrially excellent.

While the invention has been described in detail and with reference to specific embodiments thereof, it will be apparent to one skilled in the art that various changes and modifications can be made therein without departing from the spirit and scope thereof.

What is claimed is:

1. A process for preparing an optically active ketone represented by formula (I):

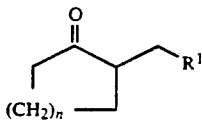
(I)

wherein R$^1$ represents a hydrogen atom or an alkyl group having from 1 to 5 carbon atoms; and n represents 1 or 2, which comprises asymmetrically hydrogenating an α,β-unsaturated ketone represented by formula (II):

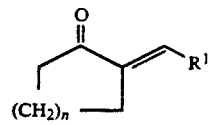
(II)

wherein R$^1$ and n are as defined above, in the presence of a ruthenium-optically active phosphine complex as a catalyst.

2. A process as claimed in claim 1, wherein said ruthenium-optically active phosphine complex is represented by formula (III):

Ru$_2$Cl$_4$(R$^2$-BINAP)$_2$(NEt$_3$)  (III)

wherein R$^2$-BINAP represents a tertiary phosphine represented by formula (IV):

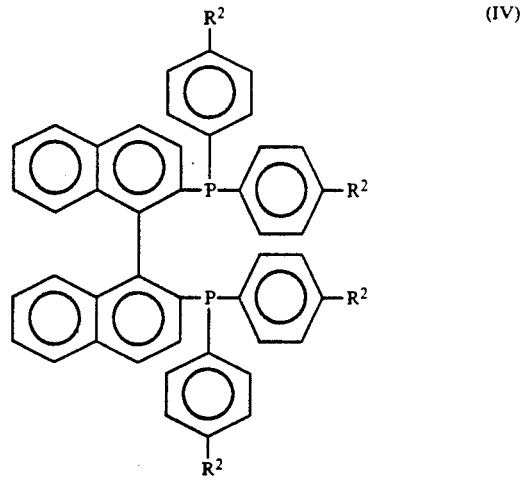
(IV)

wherein R$^2$ represents a hydrogen atom, a methyl group, or a t-butyl group; and Et represents an ethyl group.

3. A process as claimed in claim 1, wherein said ruthenium-optically active phosphine complex is represented by formula (V):

[RuX(Q)(R$^2$-BINAP)]Y  (V)

wherein R$^2$-BINAP represents a tertiary phosphine represented by formula (IV):

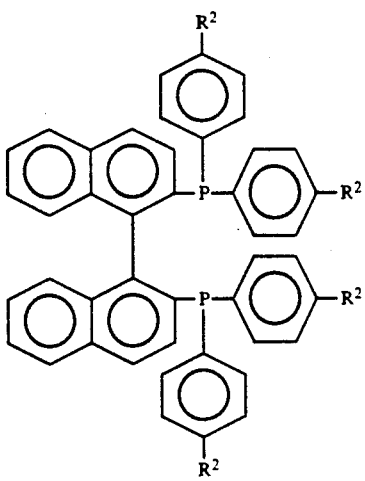

(IV)

wherein R² represents a hydrogen atom, a methyl group, or a t-butyl group; X represents a chlorine atom, a bromine atom, or an iodine atom; Q represents a substituted or unsubstituted benzene ring; and Y represents a chlorine atom, a bromine atom, an iodine atom, ClO₄, BF₄, or PF₀.

4. A process as claimed in claim 1, wherein the α,β-unsaturated ketone represented by formula (II) is selected from the group consisting of 2-methylenecyclopentanone, 2-ethylidenecyclopentanone, 2-propylidenecyclopentanone, 2-pentylidenecyclopentanone, 2-(2-methyl)propylidenecyclopentanone, 2-(3-methyl)butylidenepentanone, 2-methylenecyclohexanone, 2-butylidenecyclohexanone, 2-pentylidenecyclohexanone, 2-hexylidenecyclohexanone, 2-(2-methyl)propylidenecyclohexanone, and 2-(4-methyl)pentylidenecyclohexanone.

5. A process as claimed in claim 2, wherein the rutheniumoptically active phosphine complex of formula (III) is selected from the group consisting of Ru₂Cl(BINAP)₂(NEt₃) wherein BINAP represents 2,2'-bis(diphenylphosphino)-1,1'-binaphthyl; Ru₂Cl₄(Tol-BINAP)₂(NEt₃) wherein Tol-BINAP represents 2,2'-bis(di-p-tolylphosphino)-1,1'-binaphthyl; and Ru₂Cl₄(t-Bu-BINAP)₂(NEt₃) wherein tBu-BINAP represents 2,2'-bis(di-p-t-butylphenylphosphino)-1,1'-binaphthyl.

6. A process as claimed in claim 3, wherein said rutheniumoptically active phosphine complex of formula (V) is selected from the group consisting of [RuCl(benzene)(BINAP)]Cl, [RuCl(benzene) (Tol-BINAP)]Cl, [RuCl(p-cymene)(BINAP)Cl, [RuCl(methyl benzoate) (BINAP)]Cl, [RuBr(benzene) (BINAP)]Br, ]Br, [RuI(benzene)(Tol-BINAP)]I, [RuI(p-cymene)(BINAP)]I, [RuCl(p-cymene)(BINAP)]ClO₄, [RuCl (benzene)(BINAP)]BF₄, and ]RuI(p-cymene) (BINAP)]PF₆, wherein the phosphine derivative in each of the ruthenium-optically active phosphine complexes is either one of enantiomers thereof.

* * * * *